United States Patent
Marenzi et al.

(10) Patent No.: US 8,802,125 B2
(45) Date of Patent: Aug. 12, 2014

(54) CONTROLLED-DELIVERY SYSTEM OF PHARMACOLOGICALLY ACTIVE SUBSTANCES, PREPARATION PROCESS AND MEDICAL USE THEREOF

(75) Inventors: Gaetano Marenzi, Naples (IT); Adele Bolognese, Naples (IT); Luigi Califano, Naples (IT); Antonio Calignano, Naples (IT); Umberto Costantino, Perugia (IT); Gilberto Sammartino, Naples (IT); Vittoria Vittoria, Naples (IT)

(73) Assignee: ARIANNA Medical Devices, Rome (IT)

( * ) Notice: Subject to any disclaimer, the term of this patent is extended or adjusted under 35 U.S.C. 154(b) by 1816 days.

(21) Appl. No.: 11/996,348

(22) PCT Filed: Jul. 21, 2006

(86) PCT No.: PCT/IT2006/000556
§ 371 (c)(1),
(2), (4) Date: Jul. 29, 2008

(87) PCT Pub. No.: WO2007/010584
PCT Pub. Date: Jan. 25, 2007

(65) Prior Publication Data
US 2008/0299202 A1 Dec. 4, 2008

(30) Foreign Application Priority Data
Jul. 22, 2005 (IT) .............................. RM2005A0393

(51) Int. Cl.
*A61K 9/00* (2006.01)
*A61K 47/30* (2006.01)
*A61K 31/196* (2006.01)
*A61K 31/335* (2006.01)
*A61P 43/00* (2006.01)

(52) U.S. Cl.
USPC ........ 424/426; 424/486; 514/772.3; 514/567; 514/450

(58) Field of Classification Search
None
See application file for complete search history.

(56) References Cited

U.S. PATENT DOCUMENTS
5,466,462 A 11/1995 Rosenthal et al.

FOREIGN PATENT DOCUMENTS
EP 1 470 823 * 4/2004 ............. A61K 47/02
WO WO 2004/098574 * 5/2004 ............. A61K 9/51
WO WO 2004/098574 11/2004

OTHER PUBLICATIONS

Kalgutkar et al. "Ester and Amide Derivatives of the Nonsteroidal Antiinflammatory Drug, Indomethacin, as Selective Cyclooxygenase-2 Inhibitors". J. Med. Chem. 200, 43, 2860-2870.*
Khan et al. "Intercalation and controlled release of pharmaceutically active compounds from a layered double hydroxide". Chem Commun., 2001,2342-2343.*

* cited by examiner

*Primary Examiner* — Robert A Wax
*Assistant Examiner* — Danah Al-Awadi
(74) *Attorney, Agent, or Firm* — Gregory P. Einhorn

(57) ABSTRACT

The invention concerns a system for biocompatible drug release comprising: (i) a polymer matrix; (ii) an inorganic component located inside said matrix and characterized by a lamellar structure with a net positive or negative charge able to intercalate (iii) a pharmacologically active principle into said lamellar structure, by establishing an ionic type of bond with it and thereby obtaining an intercalation compound. The preparation process for the release system comprises the stages of: treating the lamellar solid in such a way as to give it a net positive or negative charge, then combining it with the chosen active principle, also in an ionic form, to obtain an intercalation compound which is then mixed with the polymer matrix. The release system can be employed in making medical devices, like sutures, membranes, osteosynthesis plaques, multilayered devices, gels and drug delivery systems.

26 Claims, 1 Drawing Sheet

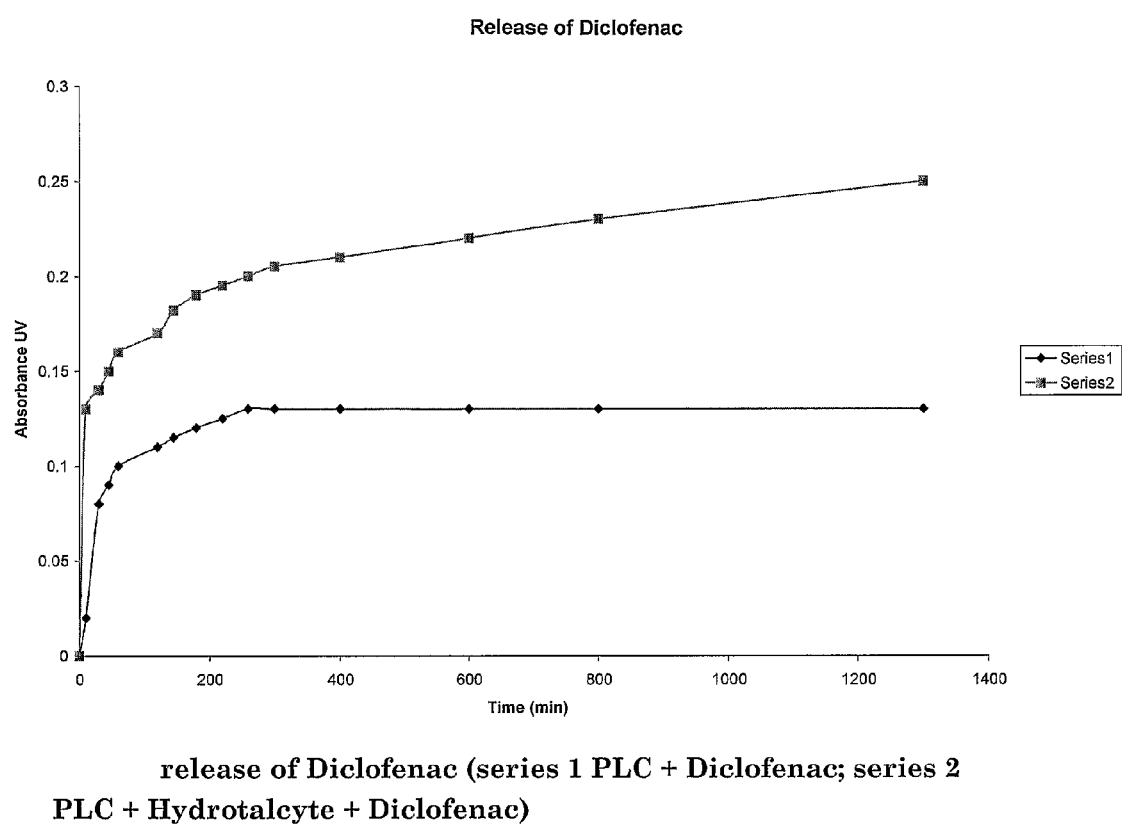
release of Diclofenac (series 1 PLC + Diclofenac; series 2 PLC + Hydrotalcyte + Diclofenac)

CONTROLLED-DELIVERY SYSTEM OF PHARMACOLOGICALLY ACTIVE SUBSTANCES, PREPARATION PROCESS AND MEDICAL USE THEREOF

FIELD OF THE INVENTION

The present invention concerns a release system for pharmacologically active substances, the preparation process and uses of the system in the medical field, in particular in the fields of repair and regeneration of tissues and surgery.

BACKGROUND ART

In the medical field, in particular in surgery, it may be of great clinical utility being able to modulate the activation of tissue repair and the regeneration processes which are at the basis of the healing processes. In this context some surgical articles of manufacture, such as, for example, sutures, membranes, osteosynthesis plaques, made of re-absorbable materials able to favour the completion of the various reparatory phases and which do not need further surgical intervention for their removal, are extremely useful. It is an advantage to load these products of manufacture with pharmacologically active substances. In fact, the possibility of local diffusion of a drug through biocompatible and re-absorbable matrixes offers the advantage of a drastic reduction of the systemically administered dose and, as a consequence, of related side-effects. A limit of these systems is the reduced capacity of ensuring an adequate local release of the drug.

There are known release systems constituted by active substances added to a polymer matrix (U.S. Pat. No. 5,466,462) or polymer matrixes possibly containing inorganic products (WO 2004/098574). The limit of these systems is the extreme velocity with which the active substance is released from the matrix and the difficulty in modulating this parameter.

In particular WO 2004/098574 foresees the addition to the matrix of powders of various either lamellar or non-lamellar inorganic solids, with the dimension of nanoparticles. The process of adding the inorganic material is not described as critical and, in the case of extrusion, foresees a simple mixing of the various components all together. Further, in the preparation example reported in WO 2004/098574 it is specified that the powders do not undergo any preliminary treatment and the three components (PEG polymers, inorganic Cloisite and the active substance, Paracetamol) are all mixed together. The resulting system is characterised by an almost total release of the active substance in an extremely short interval (60 minutes).

It is known that some lamellar solids are able to absorb and release active substances (AAPS Pharm. Sci. Tech. 2002; 3 (3) art. 26) but unfortunately as they appear in the form of microcrystalline or finely subdivided amorphous powders they do not have suitable characteristics for taking on well defined solid forms (membranes, plaques, screws, etc.). Also, the release times of the active substance are very short, in the order of 24 hours, or less (100 minutes, as reported in Int. J. of Pharmaceutics 220 (2001) 23-32).

The need was felt to have a release system able to release the active substance contained in it, with times longer than 24 hours, possibly also longer than 5 days, and, if possible, to have a release modulated over time.

SUMMARY OF THE INVENTION

It is an object of the present invention a biocompatible release system comprising: (i) a polymer matrix; (ii) an inorganic component located inside said matrix and characterised by a lamellar structure with a neutralised net positive or negative charge and able to intercalate (iii) a pharmacologically active substance into said lamellar structure by establishing a neutralising ionic type bond with it. Typically, the release system of the invention comprises about 30-99% by weight of polymer (i), preferably about 50-80% or 60-90%, more preferably about 80-90% or 80-99%; the inorganic component (ii) containing the active substance intercalated and/or absorbed on its surface is present in quantities between about 1-70% by weight, preferably about 50-20% or 40-10%, more preferably about 20-10% or 20-1%.

Preferably, the quantity of the active substance with respect to the inorganic component is given by the following expression:

Load $(g/g) = \alpha \times PM / (PF + \alpha \times PM)$ where $\alpha$ is the degree of intercalation, defined as the number of moles of active substance intercalated and/or absorbed by 1 mole of the inorganic component, PM is the molecular weight (g/mol) of the active substance, PF is the formula weight (g/mol) of the inorganic component not including the active substance.

Preferably, the active substance (iii) is present in a quantity between about 1-50% by weight, more preferably about 20-50%, most preferably about 40-50% with respect to the inorganic component. Naturally, this percentage varies with the molecular weight of the active molecule.

Another object of the invention is a release system organised in two or more superimposed layers, in which the single layers contain the same intercalation compound with the same active substance or differing intercalation compounds and active substances, possibly characterised by different release kinetics. Such a system permits the release of several active molecules in different moments, for example, an anti-inflammatory released in a short time and an antibiotic in a longer period, so as to meet the different therapeutic needs.

Another objective of the invention is the preparation process of the release system, including the stages of: treating the lamellar solid in such a way as to give it a net positive or negative charge, then combining it with the chosen active substance, the latter also being in ionic form or transformed so as to give it an ionic nature, thereby obtaining a pre-mix of intercalation compound or more generically a hybrid material, inorganic-active substance, which will then be mixed with the chosen polymer matrix. Preferably, the intercalation compound comprises 1-70% by weight of the active substance with respect to the solid, preferably 20-60% or 20-50%, more preferably 20-40% or 40-50%, even though the quantities indicated are only indicative and strictly depend on the molecular weight of the active molecule, on the nature of the active substance and of the inorganic component and on the level of intercalation, on the use of the system of the invention, and are chosen as a function of the probable pathology and the drug administration protocol.

A further object is the use of the release system of the invention to make devices to be used in the medical and veterinary field, which come into contact with, or are implanted in, or ingested by humans or animals.

Yet another object are devices made by using the system of the invention, such as, for example, sutures, membranes, osteosynthesis plaques, multilayered devices, and drug delivery systems, also with delayed delivery, which have a release optimized according to the use of the article of manufacture. Optimisation of release is both in terms of release times and in terms of the quantities of active substances released. Devices made with the release system of the invention are also characterised by mechanical properties optimized according to their final use.

Another object are articles of manufacture made or coated with the release system of the invention in single or multiple layers.

Further objects will be evident from the following detailed description of the invention.

SHORT DESCRIPTION OF THE FIGURE

FIG. 1: Release kinetics. Comparison of the release of the molecule Diclofenac incorporated directly in the single polycaprolactone polymer and the release of the same in the system of the invention, in which polycaprolactone is the matrix into which the inorganic composite hydrotalcyte, with the Diclofenac molecule anchored on its lamellae, has been dispersed.

DETAILED DESCRIPTION OF THE INVENTION

In the context of the present invention the following definitions, with the following meanings, shall be used:

Bio-compatible describes a compound or product or material which can be used in medical applications, biocompatibility can also be obtained by surface treatment of a material which in itself is not biocompatible.

Re-absorbable describes a substance which is hydrolyzed and absorbed into the organism.

Lamellar solid describes an inorganic compound not containing organic carbon which, due to its chemical structure, forms a solid which takes on a spatial configuration of a succession of lamellae, that is crystals which have a much smaller dimension than the other two dimensions (see chapter 1 of Volume VII of Comprehensive Supramolecular Chemistry, Pergamon Press, Oxford, 1996). If the lamellae have an electrical charge (positive or negative) ions of the opposite charge can be positioned inside the galleries between the lamellae, to preserve the electrical neutrality of the solid. Such ions can be substituted by active molecules in ionic form, through ion exchange reactions.

Intercalation compound describes the material which is obtained following the insertion (intercalation) of molecules or atomic or molecular ions in the inter-lamellar region of the lamellar solid.

Intercalation site is the site of the inorganic component where there is the net charge (positive or negative depending on the type of inorganic substance) which will be neutralised by the active molecule in an ionic form.

Exfoliation is the procedure which brings about the separation of the lamellae which constitute the lamellar solid in such a way that they can be considered as separate particles for the release kinetics. When exfoliation, which includes a breaking of the lamella-lamella bond, occurs in a liquid solvent, colloidal dispersion of the lamellae is obtained. When exfoliation occurs in a polymer matrix, as in the present invention, a dispersion in which the single lamellae are oriented in all directions is obtained.

Pharmacologically active substance describes a substance with pharmacological effects.

Polymer matrix describes a solid polymer which may derive from a single polymer or mixture of homo- or co-polymers, possibly partially or totally cross-linked, in which another component is located.

Drug delivery system is a release system for drugs.

Delayed delivery is a release system where the active substance is released over long and controlled periods of time.

The release system of the invention is characterised by the fact that the molecules of the pharmacologically active substances are anchored to the lamellae of an inorganic lamellar solid by ionic bonds, and the resulting lamellar solid/active substance system, also called intercalation compound, is then incorporated into a polymer matrix.

Polymers advantageously used according to the invention are the biocompatible, re-absorbable, non-re-absorbable and partially absorbable polymers. Some examples of the classes of polymers used are the following: polyethylene glycols, polycaprolactones and polyesters, polylactides, polyanhydrides, polyvinylpyrrolidones, polyurethanes, polysiloxanes, polyaminoacids, polyacrylates and polymethacrylates, polyamides, polyimides, polyanilines, polyacrylonitriles, silicons, polyether-ketones, polyether-ether-ketones, high and low density polyethylenes, polypropylenes, polystyrenes; natural polymers like polysaccharides in general, amides, celluloses, chitins, chitosans, pectins, gelatins, proteins, polypeptides; taken singularly or in mixtures, possibly functionalised and possibly partially or totally cross-linked, possibly with additives like: antioxidants, stabilisers and plasticizers; all of which are known to the experts in the field.

It has been seen that the incorporation of the intercalation compound into the polymeric matrix under the invention improves its mechanical properties (for example the elastic modulus and the breaking energy), thermal properties (for example, increasing the vitreous transition temperature and the temperature of thermal degradation of the polymer) and its permeability to liquids, gases and vapours, thereby allowing the production and elaboration of products of manufacture which have a high mechanical modulus and good tenacity.

The release system of the invention is able to release active molecules, like antibiotics, anti-inflammatories and others, in a controllable and modulated way over a wide interval, both with respects to the quantity of the molecule released and to the time-span of its release.

Further, the method of anchoring, via ionic bonds, permits release of the active molecule through ion exchange reactions, the kinetics of which depend on the concentration of the ionic bonds, of the counter-ion in the solution, on the ionic force of the solution, on the pH and on the temperature. Thus, we are in the presence of a release system that can be modulated over a wide range of situations and can be adapted to specific requests. It can be used above all in re-absorbable products of manufacture, such as for example, sutures, membranes, osteosynthesis plaques, polymer gels and devices shaped ad hoc for use in interventions on human or animal bodies, in particular in maxillo-facial surgery.

The choice of the pharmacologically active molecule depends on the application, varying from anti-microbic, antibiotic, anti-inflammatory, anti-infective agents, antigens, analgesics, growth factors etc.

Some of the molecules or active substances which may be used under the invention are listed below:

ANTIBIOTICS OF THE LACTAMIC SERIES:
PENICILLINS
ANTISTAPHYLOCOCCALS: cloxacillin, dicloxacillin, nafcillin, oxacillin;
WIDE SPECTRUM: amoxicillin, amoxicillin/clavulanic acid, piperacillin, ticarcillin
CEPHALOSPORINS
OF THE 1st GENERATION: cephydroxil, cephalexin, cephalozin,
OF THE 2nd GENERATION: cefoxitin, cefotetan, cefuroxime, cefuroxime axetil
OF THE 3rd GENERATION: cefotaxime, ceftazidime, ceftraxone, carbapenems, imipenem, cefonocid, cefatrizin
GLYCOPEPTIDES: vancomycin, teicoplanin
PHOSPHOMYCIN BACITRACIN
CYCLOSERIN
CHLORAMPHENICOL and SUCCINIC ESTERS of CHLORAMPHENICOL
TETRACYCLINES: chlortetracycline, oxytetracycline, demechlorcycline, methacycline, doxycline, monocycline
MACROLIDS: erythromycin, stearate, ustolate, clarithromycin, azithromycin, clindamycin, iosamycin, miocamycin, sisomycin, midecamycin, rokitamycin, roxithromycin, troleandomycin, spiramycin
AMINOGLYCOSIDES: streptomycin, kanamycin, amikacin, gentamycin, netilmycin, tobramycin, neomycin, spectinomycin, rifamycin
QUINOLONICS and FLUOROQUINOLONICS: nalidissic acid, norfloxacin, grapafloxacin, clinafloxacin, noxacin, levofloxacin, lomefloxacin, norfloxacin, ofloxacin, pefloxacin, sparfloxacin, ciprofloxacin, novobiocin, pipemidic acid
MISCELLANEOUS: metronidazol, mupyrocin, polymixine
NON-STEROID ANTI-INFLAMMATORIES
SALICYLATES: acetylsalicylic acid, salsalate, benorilate, sulphasalazine
DERIVATIVES OF PROPIONIC ACID: ibuprofene, naproxene, fenbufene, fenoprofene, flurbiprofene, ketoprofene, dexketoprofene, tiaprofenic, azapropazone, diclofenac, aceclofenac, diflunisal, etodolac, indomethacin, lornoxicam, mefenamic acid, nabumetone, phenylbutazone, piroxicam, sulindac, tenoxicam, tolfenamic acid, ketorolac
SELECTIVE INHIBITORS OF CYCLO-OXYGENASES II: celecoxib, etodolac, meloxicam, rofecoxib, nimesulide
IBUPROFENE
BENZAMIDINE
MYORELAXANTS OF THE SKELETAL MUSCLES: meprobamate, tizanidine, dantrolene sodium, diazepam, tiocochioside, cyclobenzaprin, pridinol, carisoprodol, metamizol
DRUGS FOR BONE PATHOLOGIES: glucosamine, clodronic acid, risedronic acid, alendronic acid, etidronic acid, ipriflavone, neridronic acid, risedronic acid, osigraft (osteogenic protein), panidronic acid, zoledronic acid
DRUGS FOR OCULAR PATHOLOGIES: carbachol, pilocarpine, dipenefrine, guanetidine, brinonidine, apraclonidine, betaxolol, carteolol, levobunolol, metipranolol, timolol, acetazolamide, brinzolamide, dorzolamide, bimatoprost, lantanoprost, travoprost, acetylcysteine
RE-EPITHELIZING SUBSTANCES: allantoin, vitamin E, vitamin A, aqueous extract of triticum vulgaris
GROWTH FACTORS: for example BMP (Bone Morphogenetic Proteins)
nutraceutics: hydro- and liposoluble vitamins, zinc sulphate, iron hydroxide
PEPTIDES, PROTEINS, POLYNUCLEOTIDES: lysozyme, platelet protein extracts, as tissue growth stimulants, peptide products from biotechnological techniques for the stimulation of growth and tissue differentiation.

The molecules indicated above can also be used, for example as esters, anhydrides, amides of succinic acid or in other ways known to the expert in the field.

Among the lamellar inorganic solids with the property of intercalation (see Chapter 1 of Volume VII of Comprehensive Supramolecular Chemistry, Pergamon Press, Oxford, 1996) according to the invention, only those which are biocompatible with negative charge of the lamellae, counterbalanced by cations positioned in the interlayer region (so-called anionic lamellar solids) and those with positive charge, counter balanced by anions positioned in the interlayer region (so called cationic lamellar solids) are to be considered within the scope of the invention (interlamellar and interlayer will be considered synonyms). Among the first ones we may mention in a non-limiting way the cationic clays (montmorillonite, vermiculite, fluoroectorite, bentonite) and the phosphates of zirconium and titanium, which are able to intercalate, through a process of cation exchange, active substances containing a site which can be converted into a cation in their molecules, generally an amine site able to give a quaternary ammonium cation. Among the latter, there are considered the synthetic hydrotalcytes, also known by the name of anionic clays or double lamellar hydroxides (referring to the two cations present in the layers, for example $Mg_6Al_2(OH)_{16}CO_3$, which can intercalate active substances with sites which can; give anions, typically carboxyl, phenolic, sulphonic and phosphonic groups, through a process of anion exchange. The chosen matrixes for the intercalation of anionic type drugs are the synthetic hydrotalcytes of Mg—Al or Zn—Al types with a molar ratio Mg(Zn)/Al which varies from 1.5 to 4 and with an anionic exchange capacity which varies from 2 to 5 mequiv/g.

In the case of the hydrotalcytes the lamellar solid derives from brucite $Mg(OH)_2$ by Mg/Al substitution, which creates an excess of positive charge, compensated by anions present in the galleries (for example $Cl^-$ o $NO_3^-$). The charge depends on the extent of the Mg/Al substitution and is expressed as a density of charge, which determines the capacity of anionic exchange (mequiv/g). The general formula of the synthetic hydrotalcytes or double lamellar hydroxides can be written as the general formula (I):

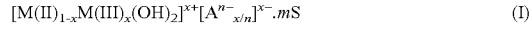

$$[M(II)_{1-x}M(III)_x(OH)_2]^{x+}[A^{n-}_{x/n}]^{x-}.mS \qquad (I)$$

where M(II) is a metal of valence (II) preferably chosen from Mg, Zn, Co, Ni, Mn, Cu.; M(III) is a metal of valence (III) preferably chosen from Al, Cr, Fe, V, Co; $A^{n-}$ is an anion loaded with the negative charge n, which compensates the overall charge and is preferably chosen among $Cl-$, $NO_3-$, $CO_3--$, $SO_4-$, and organic anions; m is the number of molecules of solvent, generally water, co-intercalated (S), by formula weight of the compound. The number of moles x of the cation M(III) by formula weight of the compound generally varies from 0.2 to 0.40 and its value determines the density of the charge of the layer and the capacity of anionic exchange. The number of moles of the co-intercalated solvent, m, is normally between 0 and 2, depending on the nature of A and the degree of intercalation (for example 0.6 $H_2O$). Compounds of hydrotalcytes and similar systems in which, in the interval of x considered, there are several bivalent cations (for example Mg and Cu) or several trivalent cations (for example Al and Cr) are considered. Again, according to the invention, the double hydroxide with the formula $Al_2Li(OH)_2A^{n-}_{1/n}$ is considered a lamellar inorganic component. The anions present in the gallery can be substituted, by ionic exchange reactions, with organic molecules bearing a negative charge (for example carboxyls, sulphonates and phosphonates).

Surprisingly, it has been found that when the intercalation compound is dispersed at a micro- or nano-meter level in the polymer matrix the kinetics of the drug release, in the conditions described by the FUI, Farmacopea Ufficiale Italiana, are Very much slower than those of the active molecule alone, which is dispersed in the polymer as a microcrystalline powder. It is believed that the release process requires the diffusion of the active substance in the ionic form from the lamellar solid to the polymer matrix and from this towards the outside, with the contemporaneous retrodiffusion of ions of the same sign which diffuse from the outside into the polymer and exchange with the active substance. This established mechanism is regulated by various parameters (temperature, concentration and nature of the ions which substitute the drug, disposition of the intercalation compound in the polymer, its concentration and the nature of the drug and of the polymer) the control of which permits varying the velocity of release. The release times can be modulated according to the active substance, the lamellar solid and the polymer matrix chosen, and can even be of 24 hours or more, even above five days, and reaching times of 20-30 days or more is easily possible.

The preparation method for the release system is a multi-stage process which foresees the preparation of a pre-mix including the inorganic lamellar solid and the active substance. The pre-mix, preferably in micro- and nano-particle form, is then mixed with the polymer matrix following known techniques.

The preparation of the pre-mix or inorganic lamellar solid/active substance hybrid material comprises the stage of anchoring the molecules of the pre-selected active pharmacological substances in the galleries of the inorganic lamellar solid (complex molecule-inorganic solid, also indicated as intercalation compound). The process is carried out following the known procedures, as for example described in AAPS Pharm. Sci. Tech. 2002; 3 (3) art. 26, which lead to the dispersion of the powder of the chosen lamellar solid in a solution containing the active substance in ionic form. The exchange normally occurs under stirring of the solution at the pre-selected temperature and using volumes of solutions and concentrations suitable for obtaining the partial or total exchange of the ions present in the initial solid with the active substance. An example of preparation of an intercalation compound under the invention is described in Example 1. The state of the art suggests that lamellar solid/active substance complexes in which the lamellar solid is synthetic hydrotalcyte can also be obtained with the procedures known as direct precipitation, that is, precipitation of the double hydroxides in the presence of the active substance in an anionic form, and reconstruction of the lamellar structure starting from mixed oxides in an aqueous solution which contains the active substance (see: F. Cavani, F. Trifiro, A. Vaccari, Catal. Today, 11 (1991) 173).

The intercalation compound can be characterised by thermo-gravimetric measurement, which provides the quantity of inorganic residue after the thermal degradation at 800° C. The difference gives the quantity of the active substance present in the mix; X-ray diffractometric analysis provides confirmation of the intercalation of the active molecule.

The choice of the inorganic solid is made as a function of the polymer matrix and above all of the type of active molecule. Once the bioactive organic molecule is chosen the parameters which can vary are:

1. type of inorganic lamellar solid. Solids with negatively charged lamellae (smectic clays, lamellar phosphates of Zr(Ti)) shall be used for active substances of the cationic type, solids with positively charged lamellae (natural and synthetic hydrotalcytes) shall be used for anionic active substances. Both types of solid appear in the form of microcrystalline powder of dimensions which can vary typically in the interval of about 0.01-100 µm or 1-50 µm, preferably 0.1-10 µM or 30-50 µM.

2. Density of charge. This parameter is of interest in particular regarding the synthetic hydrotalcytes which can be synthesized according to the state of the art with different M(III)/M(II) ratios and therefore with different charge densities from which different loads of the active substance (from 2 to 5 or 2 to 4 mmol/g) and of the inorganic solid are obtained, thus allowing modulable loading. The different M(III)/M(II) ratio is obtained by varying the stoichiometry of the preparation reaction of the hydrotalcytes. As described herein above, the insertion of the trivalent cation in the lamella at the moment of the synthesis determines an excess of positive charge (each trivalent cation confers an elementary positive charge) which must be balanced by anions present in the interlamellar region, under the invention these anions are, preferably, active substances. The charge density can be varied by varying the parameter x in the general formula (I) reported above. Different charge densities determine different loadings of the active substance when one considers the maximum level of intercalation. This is measured by making an elemental analysis of magnesium and aluminium. Since the M(III)/M(II) ratio determines the positive charge of the inorganic lamellae and since the ratio can vary, the quantity of ions with the opposite charge must vary as a consequence. This makes the quantity of the active molecule modulable, and the maximum loading corresponds to the maximum substitution of the counter-ions.

3. Extension of the ionic exchange reaction which gives rise to a different percentage of exchange and different loading of active substance. It is so possible to exchange only a part of the anions already present in the lamellar solid with the active substance. If, for example, the loading on the lamellar is 0.37 moles per total moles, one may load the active molecule up to a maximum of 0.37, with the possibility of stopping at lower values (for example 0.20 moles per total moles).

Once the intercalation compound has been prepared it is incorporated into the chosen matrix polymer. Said matrix polymer can be biodegradable or non-biodegradable, according to the use and can also be a copolymer or a mixture of polymers and/or copolymers, as previously indicated. The biodegradable and re-absorbable polymers are preferred for uses in which non-removal from the patient's body after use is preferred. Further, their erosion and absorption being linked to the kinetics of hydrolysis, the use of a system with different kinetics of hydrolysis allows release in time periods that can be modulated, from a few hours to many months and longer. For example, PEO hydrolizes in water in a few hours, releasing all the active principle, while PCL hydrolizes in time periods longer than a year. Therefore intermediate times can be obtained mixing the two polymers.

In general the release kinetics seen have two stages: a first fast stage, which can last from a few minutes to a few hours and a second slower stage in which the release varies linearly with time.

The parameters to take into consideration in the preparation of the release system under the invention are:
a) type of polymer system;
b) concentration of the intercalation compound in the polymer matrix. Such concentration can advantageously vary from 0.1% to 40% by inorganic weight of active molecule content;
c) type of incorporation process, the conditions of which are chosen by the expert in the field according to his knowledge:
by solvent, via casting;
by melting, via pressure fusion or extrusion;
by ball milling (mixing in a mill with rigid spheres);
by sonication (Ref. Michael Alexandre, Philippe Dubois, Materials Science and Engineering, 28 (2000) 1-63; Sorrentino, Andrea; Gorrasi, Giuliana; Tortora, Mariarosaria; Vittoria, Vittoria; Costantino, Umberto; et. al. Polymer Volume: 46 (2005) pp. 1601-1608).

Once the release system of the invention is obtained, this can undergo further manipulation to obtain the desired end-products.

Some of the techniques and final products are herein indicated by way of example and are accessible to the experts in the field:

Compact and porous membranes, can be obtained by pressure fusion or via casting by solvent;

sutures can be obtained by extrusion of the melted polymer;

injectable gels can be obtained by gel formation in an appropriate solvent;

sponges can be obtained from solvent-non-solvent mixtures and by insufflation of inert gases;

plaques can be obtained by pressure fusion;

specific products of manufacture with a predefined form can be obtained by injection moulding in the required shape or by turning;

multilayered products of manufacture.

The parameters from which the release kinetics of the active molecules depend can be modulated and controlled in a wide range, and both according to the indications given in the description and to his personal knowledge, the expert in the field will be able to find the most appropriate conditions for carrying out the invention. In general, the aspects that are to be evaluated are:

the type of active molecule;

the type of inorganic material onto which the active molecule is anchored, by strong (ionic) or weak bonds;

the type of polymer matrix, including homopolymers, copolymers or mixtures;

the concentration of the active molecule anchored to the inorganic compound;

the concentration of the complex (active molecule-non organic) in the polymer matrix;

the type of product of manufacture (compact or porous).

It is clear, therefore, that by choosing and controlling in the right way the above mentioned parameters it is possible to produce membranes, sutures, gels and devices suitable for a number of applications in the biomedical field and for the controlled release of drugs.

Further, depending from the percentage of lamellar solid in it, the system of the invention unexpectedly gets mechanical properties (increase in the resistance to compression, to temperature, to traction, increase in mouldability also into complex shapes) while maintaining the release mode unchanged, this being a function of the surface exposed to the solubilizing action of biological fluids. The improved physical properties of the invention also allow obtaining devices with a concentric stratification, with the ability to release different substances for different periods of time based on their surface and concentration in the lamellar solid, thereby enabling the administration of several pharmacological treatments in a single application. The controlled release, prolonged in situ, allows using reduced amounts of systemic drugs, a better local control of bacterial/inflammatory phenomena and their functioning, optimising both the professional clinical intervention and the pharmacological therapy in patients with a low compliance. This additional value of the system of the invention is of particular relevance in those patients where multiple pathologies of the hepatic or renal systems which make the application of an effective systemic therapy difficult. Further, reduced local concentrations of the drug, though maintaining their therapeutic effectiveness, allow the intake of drugs which, if administered by the same route, would give rise to pharmacokinetic interference phenomena. The system according to the invention allows, among other things, mono- or multi-layered coating of the surfaces of orthopedic prostheses and/or of implanted screws used in the medical practice, especially in dental and maxillofacial surgery and suitably loaded with active principles aimed to promoting the osteointegration which is at the basis of the success of the rehabilitative and reconstructive surgical therapy. For example, coating the implant screws used in maxillofacial and oral surgery, and loading the matrix with molecules and substances able to activate osteoblasts (and/or inhibit osteoclasts) to favour new bone formation around the screw in shorter times, could be conceived. Clinically speaking, this could mean a reduction of normal healing times and of osteointegration and the possibility of much more rapid and secure functionalization (prosthesis loading).

The following are given by way of example to illustrate the invention and are not to be considered as limiting its scope.

Example 1

Solid urea was added to a 0.5 mol/dm$^3$ solution of metal chlorides, with a molar ratio, M(III)/[M(III)+M(II)], equal to 0.33, until the molar ratio urea/[(III)+M(II)] reached the value of 3.3. The clear solution was heated, under stirring, to a temperature between 60 and 100° C. All the materials collected showed X-ray diffractograms typical of compounds belonging to the hydrotalcyte (HTlc) family, the general formula of which can be written as $[M(II)_{1-x}M(III)_x(OH)_2]^{x+}[A^{n-}_{x/n}]^{x-}.mS$, where M(II) can be Mg, Zn, Co, Ni, Mn etc.; M(III) can be Al, Cr, Fe, V, Co, etc.; $A^{n-}$ is the anion which compensates the charge and can be Cl-, $NO_3$-, $CO_3$--, $SO_4$-, organic anions, etc.; m is the number of molecules of the co-intercalated solvent (S) by formula weight of the compound. The number of moles x of the cation M(III) by formula weight of the compound generally varies between 0.2 and 0.33 and its value determines the charge density of the layer.

In the current example we obtained a compound with the formula: $[Mg_{0.65} Al_{0.35}(OH)_2] (CO_3)_{0.175} 0.68H_2O$ as determined by elemental analysis (Sample A).

Sample A was titrated with HCl 1 M in a solution of NaCl 1 M. 15 g of sample A were extracted and suspended in 300 ml of a solution of NaCl 1M. The suspension was titrated in a pHstat and kept under agitation for 24 hours. Successively it was centrifuged and the wet solid was washed three times with distilled water and dried in an oven. The crystalline solid was analysed by X-ray to control the exchange occurred between carbonate and chloride. Elemental analysis demonstrated that the compound (Sample B) was obtained: $[Mg_{0.65} Al_{0.35}(OH)_2] Cl_{0.35} 0.68 H_2O$. 14.2 grams of sample B were obtained.

Example 2

8.67 g of Diclofenac (DIK) were added to a solution containing 135 ml of decarbonated water and 135 ml of ethyl alcohol EtOH. 5 g of compound B were added and the temperature was raised to 80° C. The suspension was left under stirring for 24 hours and then brought to room temperature. It was then centrifuged and the intercalation of the DIK occurring in the lamellae of hydrotalcyte was checked by x-ray in the wet solid. The wet solid was then washed three times with a solution of cold decarbonated water and ethanol (in a 1:1 ratio) and then dried in a dryer. 12 g of the compound of formula: $[Mg_{0.65} Al_{0.35}(OH)_2] DIK_{0.35} 0.68 H_2O$, were obtained (Sample C).

Example 3

10 g of polycaprolactone (PCL) were dissolved in 100 ml of tetrahydrofurane (THF) and kept under stirring. 1 g of sample C was suspended in 100 ml of a mixture of tetrahydrofurane and methanol (2:8) and added to the previous mixture. The suspension was left under stirring for 24 hours. The solvent was removed by evaporation and subsequent drying in an oven. 11.5 g of solid sample made of a mixture of PCL and hydrotalcyte in which diclofenac is intercalated (Sample D) were obtained. The concentration of hydrotalcyte containing diclofenac was 10%. Different concentrations were obtained mixing 100 mg, 200 mg, 500 mg of sample C with 10 g of PCL, obtaining concentrations of 1%, 2% and 5%.

Example 4

To carry out release tests, a sample of PCL with 1% diclofenac not anchored to the hydrotalcyte was prepared for comparison (Sample E). From samples D (PCL with 2% of hydrotalcyte containing diclofenac) and E (PCL containing 1% of diclofenac) two squares of 1 cm by each side were cut, weighing 23 mg and 22.5 mg respectively. It is important to note that the percentage concentrations of diclofenac in the two samples were the same (1%). The two samples were immersed in 20 ml of saline and, at determined times, the liquid in contact with the samples was put in a UV spectrophotometer (Perkin Elmer) and the absorbance was determined, corresponding to the absorption wavelength of the molecule of diclofenac. Absorbance is proportional to the concentration of the active molecule, according to the formula:

$$A = \epsilon c l$$

where c is the concentration, $\epsilon$ and l are constant. The increase of absorbance is, therefore, directly related to the increase in the concentration of diclofenac which passes from the solid polymer matrix into the saline. The FIGURE shows the trend of absorbance for sample E (series 1) (PLC with diclofenac) and sample D (series 2) (PCL with hydrotalcyte and diclofenac). In series 1, the release of 90% of the active substance was obtained at 70 minutes, while in series 2 a release of 64% was obtained in the same time period.

It can be noted that, when the active molecule is not anchored to the hydrotalcyte, it is released rapidly, and the complete release is reached after 200 minutes of contact with the solution, while in the other case the release is much slower. Moreover, in the first case a smaller quantity of the active molecule is released. The FIGURE also shows an initial fast release stage for the system of the invention, which also ends at around 200 minutes, and a second, slow, stage which continues with a linear release over time. This two-stage effect, generally present in the release system of the invention, constitutes an added effect of great interest, since it allows an initial peak at the time of greatest need for the drug and a subsequent gradual release for maintenance. Further, two important phenomena were observed, which constitute a further advantage of the system according to the invention, i.e. the anchoring of the active molecule onto the inorganic lamellar compound allows: a slower release; the release of a greater number of molecules. This makes the system of the invention much more efficient.

Example 5

1 g of sample D was put in between two leaves of Teflon and brought to 70° C. in a heating press. The sample % was then left for 30 seconds at the temperature of 70° C. to allow the melting of the polycaprolactone (PCL) and then the pressure between the plates was taken to 1.15 bars for 1 minute. After this time the sample was brought back to atmosphere pressure and rapidly cooled in the air. A compact membrane of 0.010 cm of thickness (Sample F) was obtained. Varying the pressure or placing sample D in between two leaves of Teflon with a spacer leaf of controlled thickness provided with a window to locate the sample, membranes of variable thickness can be obtained at wish.

Example 6

1 g of sample D was suspended in tetrahydrofurane and stirred for 6 hours. It was then put in a Petri dish and the solvent was rapidly evaporated to thus obtain a porous membrane (Sample G). The porosity of the membrane can be varied by varying the evaporation rate or by using a non-solvent with an inversion of phase process.

Example 7

1 g of sample D was put into a syringe and the temperature raised to 70° C. A slight pressure of the plunger allows a liquid sample to come out of the needle and to become solid at room temperature while it is drawn and wound like a thread. In the present example the thread was obtained at a speed of 1 cm/s and had a section of 0.0005 cm. The thread showed good mechanical properties, like the elastic modulus (400 Mpa) and the breaking force (60 Mpa).

Threads with different sections can be produced by varying the section of the exit nozzle and the speed of sample drawing before solidification.

The invention claimed is:

1. A biocompatible delayed release system comprising:
(i) a polycaprolactone polymer matrix, wherein the biocompatible delayed release system comprises about 30% to 90% by weight of polymer matrix, and the polymer matrix formulated as a lamellar charged structure; and
(ii) an intercalation compound dispersed inside the polycaprolactone polymer matrix, wherein the intercalation compound comprises:
(a) an inorganic hydrotalcyte component having a lamellar structure with a neutralized net positive or negative charge; and
(b) a diclofenac intercalated within said hydrotalcyte lamellar structure and having an ionic bond with the inorganic hydrotalcyte component,
wherein the intercalated combination of the inorganic hydrotalcyte component and of the diclofenac constitutes the intercalation compound,
and the diclofenac is present in a quantity ranging from between about 1% to 50% by weight as compared to the inorganic hydrotalcyte component,
and the concentration of the intercalation compound in the biocompatible delayed release system is between about 1% and 10%, and wherein the delayed release system has a two stage release profile.

2. The delayed release system of claim 1, wherein the biocompatible delayed release system is formed as a porous membrane.

3. The delayed release system of claim 1, wherein the diclofenac is intercalated and absorbed on the surface of the lamellae.

4. The delayed release system of claim 1, wherein the amount of diclofenac compared to the amount of inorganic hydrotalcyte component is determined by the following expression:

$$\text{Loading (g/g)} = \alpha \times PM/(PF + \alpha \times PM)$$

where α is the intercalation rate, defined as the number of moles of active substance intercalated and/or absorbed onto 1 mole of the inorganic component, PM is the molecular weight (g/mol) of the active substance, PF is the formula weight (g/mol) of the inorganic component comprising the active substance.

5. The delayed release system of claim 1, wherein the diclofenac is present in quantities ranging between 20% to 50% by weight compared to the inorganic component.

6. The delayed release system of claim 1, wherein the concentration of the intercalation compound in the biocompatible delayed release system is about 10%.

7. The delayed release system of claim 1, wherein the biocompatible delayed release system is formulated to be taken individually or in a mixture.

8. The delayed release system of claim 7, wherein the biocompatible delayed release system further comprises one or more antioxidants, stabilisers, or plasticizers.

9. The delayed release system of claim 1, wherein the biocompatible delayed release system further comprises an active substance selected from the group consisting of antimicrobics, antibiotics, anti-inflammatories, anti-infectives, antigens, analgesics and growth factors.

10. The delayed release system of claim 1, wherein the biocompatible delayed release system further comprises an active substance selected from the group consisting of: antibiotics of the β-lactamic series; non-steroid anti-inflammatories; myorelaxants of the skeletal muscles, meprobamate, tizanidine, dantrolene sodium, diazepam, tiocochioside cyclobenzaprin, pridinol, carisoprodol metamizol; drugs for bone pathologies, glucosamine, clodronic acid, risedronic acid, alendronic acid, etidronic acid, ipriflavone, neridronic acid, risedronic acid, osigraft (ostrogenic protein), panidronic acid, zoledronic acid; drugs for ocular pathologies, carbachol, pilocarpine, dipenefrine, guanetidine, brinonidine, apraclonidine, betaxolol, carteolol, levobunolol, metipranolol, timolol, acetazolamide, brinzolamide, dorzolamide, bimatoprost, lantanoprost, travoprost, acetylcysteine; Re-epithelizing substances, allantoin, vitamin E, vitamin A, aqueous extract of triticum vulgaris; growth factors, BMP (Bone Morphogenetic Proteins); nutrient factors, hydro-and lipo-soluble vitamins, zinc sulphate, iron hydroxide; peptides, lysozyme, platelet protein extracts, tissue growth stimulants, peptide products from biotechnology techniques for growth stimulation or for tissue differentiation, proteins, polynucleotides, corresponding derivatives and pharmacologically acceptable salts thereof.

11. The delayed release system of claim 10, wherein the antibiotics of the β-lactamic series are selected from the group consisting of: penicillins, anti-staphylococcal penicillins, cloxacillin, dicloxacillin, nafcillin, oxacillin; wide spectrum penicillins, amoxicillin, amoxicillina/clavulanic acid, piperacillin, ticarcillin; cephalosporins in general, cephalosporins of the 1st generation, cephadroxil, cephalexin, cephalozin; cephalosporines of the 2nd generation, cefoxitin, cefotetan, cefuroxime, cefuroxime acetyl; cephalosporines of the 3rd generation, cefotaxime, ceftazidime, ceftraxone, carbapenems, imipenem, cefonocid, cefatrizin; glycopeptides, vancomycin, teicoplanin; phosphomycin; bacitracin; cycloserin; chloramphenicol and succinic acid esters of chloramphenicol; tetracyclines, chlortetracycline, oxytetracycline, demechlorcycline, methacyclin, doxicline, monocycline; macrolids, erythromycin, stearate, ustolate, clarythromycin, azithromycin, clindamycin, iosamycin, miocamycin, sisomycin, mideaamycin, rokitamycin, roxithromycin, troleandomycin, spiramycin; aminoglycosides, streptomycin, kanamycin, amikacin, gentamycin, netilmycin, tobramycin, neomycin, spectinomycin, rifamycin; quinolonics e fluoroquinolonics, nalidissic acid, norfloxacin, grapafloxacin, clinafloxacin, noxacin, levofloxacin, lomefloxacin, norfloxacin, ofloxacin, pefloxacin, sparfloxacin, ciprofloxacin, novobiocin, pipemidic acid, metronidazol; mupirocin; and polymixin.

12. The delayed release system of claim 10, wherein the non-steroid anti-inflammatories are selected from the group consisting of: salicylates, acetylsalicylic acid, salsalate, benorilate, sulphasalazine; derivatives of propionic acid, ibuprofene, naproxene, fenbufene, fenoprofene, flurbiprofene, ketoprofene, dexketoprofene, tiaprofenic, azapropazone, diclofenac, aceclofenac, diflunisal, etodolac, indomethacin, lornoxicam, mefenamic acid, nabumetone, phenylbutazone, piroxicam, sulindac, tenoxicam, tolfenamic acid, ketorolac; selective inhibitors of cyclo-oxygenase II, celecoxib, etodolac, meoxicam, rofecoxib, nimesulide; ibuprofene; and benzamidine.

13. The delayed release system of claim 1, wherein the diclofenac is derivatized to an ester, an anhydride, an amide, a succinic acid amide, a carboxylate, a sulphonate, or a phosphonate.

14. The delayed release system of claim 1, wherein the inorganic hydrotalcyte compound is intercalated with a negatively charged lamellae, counterbalanced by cations located in an interlamellar region.

15. The delayed release system of claim 14, wherein the cations in the interlamellar region comprise a cationic clay selected from the group consisting of a montmorillonite, a vermiculite, a fluoroectorite, a bentonite, and a phosphate of a zirconium or a titanium.

16. The delayed release system of claim 1, wherein the hydrotalcyte comprises a synthetic hydrotalcyte.

17. The delayed release system of claim 1, wherein the lamellar charged structure is derived from a brucite $Mg(OH)_2$ by substitution of a Mg with an Al.

18. The delayed release system of claim 16, wherein the synthetic hydrotalcyte are of a Mg—Al or a Zn—Al type with a molar ratio of Mg(Zn)/Al which varies from 1.5 to 4 and with an anionic exchange capacity which varies from 2 to 5 mequiv/g.

19. The delayed release system of claim 16, wherein the synthetic hydrotalcyte are represented by the following general formula (I):

$[M(II)_{1-x}M(III)_x(OH)_2]^{x+}[A^{n-}_{x/n}]^{x-} \cdot mS$ (I) where M(II) is a metal of valence (II) selected from the group consisting of Mg, Zn, Co, Ni, Mn, Cu.; M(III) is a metal of valence (III) selected from the group consisting of Al, Cr, Fe, V, Co; $A^{n-}$ is an anion with negative charge n, which compensates the charge and is selected from the group consisting of Cl–, $NO_{3-}$, $CO_{3--}$, $SO_{4--}$, organic anions; m is the number of molecules of the co-intercalated solvent (S) or water, and is between 0 and 2, by formula weight of the compound; the number of moles x of the cation M(III) by formula weight of the compound varying from 0.2 to 0.40.

20. The delayed release system of claim 1, wherein the hydrotalcyte is the double hydroxide of the formula $Al_2Li(OH)_2A^{n-}_{1/n}$.

21. The delayed release system of claim 1, wherein the intercalation compound is dispersed at a micro- or a nanometer level in the polycaprolactone polymeric matrix.

22. The delayed release system of claim 1, wherein the release rate of the diclofenac is 24 hours or more.

23. A product of manufacture comprising the biocompatible delayed release system of claim 1.

24. A product of manufacture comprising the biocompatible delayed release system of claim 1, wherein the product of manufacture is manufactured as a suture, an osteosynthesis plaque, a gel, a sponge, an implant screw or an orthopedic prosthesis.

25. The biocompatible release system of claim 1, formulated as a surface coating for a product of manufacture.

26. The biocompatible release system of claim 1, wherein the polymer matrix further comprises a biocompatible, reabsorbable, non-reabsorbable, partially reabsorbable polymer selected from the group consisting of polyethylene glycols, polyesters, polylactides, polyanhydrides, polyvinylpyrrolidones, polyurethanes, polysiloxanes, polyamminoacids, polyacrylates and polymethacrylates, polyamides, polyimides, polyanilines, polyacrylonitriles, silicons, polyether-ketones, polyether-ether-ketones, high and low density polyethylenes, polypropylenes, polystyrenes; polysaccharides, amides, celluloses, chitins, chitosans, pectins, gelatins, and a mixture thereof.

\* \* \* \* \*